(12) United States Patent
Cao et al.

(10) Patent No.: US 9,921,187 B2
(45) Date of Patent: Mar. 20, 2018

(54) REAL-TIME PAVEMENT PROFILE SENSING SYSTEM USING AIR-COUPLED SURFACE WAVE

(75) Inventors: Yinghong Cao, Malden, MA (US); Ming Wang, Melrose, MA (US)

(73) Assignee: Northeastern University, Boston, MA (US)

( * ) Notice: Subject to any disclaimer, the term of this patent is extended or adjusted under 35 U.S.C. 154(b) by 1014 days.

(21) Appl. No.: 13/980,013

(22) PCT Filed: Jan. 20, 2012

(86) PCT No.: PCT/US2012/022016
§ 371 (c)(1),
(2), (4) Date: Jul. 16, 2013

(87) PCT Pub. No.: WO2012/100153
PCT Pub. Date: Jul. 26, 2012

(65) Prior Publication Data
US 2013/0289896 A1    Oct. 31, 2013

Related U.S. Application Data

(60) Provisional application No. 61/434,522, filed on Jan. 20, 2011.

(51) Int. Cl.
*G01B 3/00* (2006.01)
*G01B 5/00* (2006.01)
(Continued)

(52) U.S. Cl.
CPC .............. *G01N 29/11* (2013.01); *E01C 23/01* (2013.01); *G01V 1/303* (2013.01); *G01N 2291/044* (2013.01)

(58) Field of Classification Search
None
See application file for complete search history.

(56) References Cited

U.S. PATENT DOCUMENTS 4,809,239 A * 2/1989 Esmersoy .............. G01V 1/303
367/33
5,095,465 A * 3/1992 Stokoe, II ............ G01N 29/041
367/14
(Continued)

FOREIGN PATENT DOCUMENTS

WO   WO-2012/019315 A1   2/2012
WO   WO 2012100153 A1 *  7/2012   ............. G01V 1/303

OTHER PUBLICATIONS

Cao et al, "A Fast Inversion Analysis Algorithm for the Spectral Analysis of Surface Wave (SASW) method," Mar. 6, 2011, Nondestructive Characterization for Composite Materials, Aerospace Engineering, Civil Infrastructure and Homeland Security 2011.*
(Continued)

*Primary Examiner* — Roy Y. Yi
*Assistant Examiner* — Leonard S Liang
(74) *Attorney, Agent, or Firm* — Posternak Blankstein & Lund LLP

(57) ABSTRACT

A non-contact testing system and method using acoustic sensors and a mobile sensing system using this system and method is disclosed. The leaky surface wave is recorded with directional microphones. A fast inversion analysis algorithm is introduced to estimate the shear velocity profile and elastic modulus for the subsurface layers of pavement structures, using the dispersion curves obtained from the acoustic signals. An electrical hammer is used to produce impact impulses automatically. A mobile sensing system is integrated on a mobile cart to perform the mobile subsurface sensing for pavement structures.

22 Claims, 11 Drawing Sheets

(51) Int. Cl.
  *G01N 29/11* (2006.01)
  *G01V 1/30* (2006.01)
  *E01C 23/01* (2006.01)

(56) References Cited

U.S. PATENT DOCUMENTS

| | | | | |
|---|---|---|---|---|
| 5,587,968 A * | 12/1996 | Barr | .................. | G01V 1/303 367/54 |
| 5,614,670 A * | 3/1997 | Nazarian | .................. | E01C 23/00 73/146 |
| 5,983,701 A * | 11/1999 | Hassani | .................. | G01N 3/307 73/12.01 |
| 6,584,414 B1 * | 6/2003 | Green | .................. | G01N 33/42 701/408 |
| 7,440,357 B2 | 10/2008 | Hopperstad | | |
| 7,813,224 B2 * | 10/2010 | Krumhansl | .................. | G01V 1/147 181/121 |
| 8,121,823 B2 * | 2/2012 | Krebs | .................. | G01V 1/28 703/10 |
| 8,223,587 B2 * | 7/2012 | Krebs | .................. | G01V 1/282 367/43 |
| 8,400,168 B2 * | 3/2013 | Troxler | .................. | G01N 22/00 324/637 |
| 8,537,638 B2 * | 9/2013 | Lee | .................. | G01V 1/368 367/73 |
| 2004/0223411 A1 * | 11/2004 | Vossen | .................. | G01V 1/28 367/38 |
| 2004/0244490 A1 * | 12/2004 | Turner | .................. | G01N 29/07 73/587 |
| 2005/0143924 A1 * | 6/2005 | Lefebvre | .................. | G01V 1/284 702/18 |
| 2010/0270026 A1 * | 10/2010 | Lazaratos | .................. | G01V 1/28 166/369 |
| 2010/0286921 A1 * | 11/2010 | Lee | .................. | G01V 1/28 702/17 |
| 2011/0090760 A1 * | 4/2011 | Rickett | .................. | G01V 1/282 367/73 |

OTHER PUBLICATIONS

Zomorodian et al, "Inversion of SASW dispersion curves based on maximum flexibility coefficients in the wave number domain," Dec. 3, 2005, Soil Dynamics and Earthquake Engineering.*

Ryden et al, "Fast simulated annealing inversion of surface waves on pavement using phase-velocity spectra," Jul. 5, 2006, Geophysics, vol. 71, No. 4.*

Picozzi et al, "Combining genetic and linearized algorithms for a two-step joint inversion of Rayleigh wave dispersion and H/V spectral radio curves," Nov. 2, 2006, Geophys. J. Int. (2007) 169, 189-200.*

Pezeshk et al, "A New Inversion Procedure for Spectral Analysis of Surface WAves Using a Genetic Algorithm," Oct. 2005, Bulletin of the Seismological Society of America, vol. 95, No. 5, pp. 1801-1808.*

Gartin, R.S., "An Introduction to Wave Propagation in Pavements and Soils: Theory and Practice," State of Alaska, Department of Transportation and Public Facilities, Fairbanks, Alaska, 43 pages (Feb. 1991).

International Search Report and Written Opinion issued by the U.S. Patent and Trademark Office as International Searching Authority for International Application No. PCT/US2012/022016 dated May 23, 2012 (10 pages).

Ryden, et al., "Non-contact Surface Wave Testing of Pavements Using a Rolling Microphone Array," NDTCE'09, Non-Destructive Testing in Civil Engineering, Nantes, France, 6 pages (Jun. 30-Jul. 3, 2009).

Shirazi, Hamid, "Implementation of artificial neural networks to automate spectral-analysis-of-surface-waves method," Department of Civil Engineering, The University of Texas at El Paso, 162 pages (Aug. 2005).

Zhu, J. and Popovics, J. S., "Non-contact NDT of Concrete Structures Using Air Coupled Sensors," Department of Civil and Environmental Engineering, University of Illinois at Urbana-Champaign, NSEL Report Series, Report No. NSEL-010, 119 pages (May 2008).

* cited by examiner

REAL-TIME PAVEMENT PROFILE SENSING SYSTEM USING AIR-COUPLED SURFACE WAVE

CROSS REFERENCE TO RELATED APPLICATIONS

This application is a national stage entry under 35 U.S.C. § 371 of international application No. US12/22016, filed Jan. 20, 2012, entitled "Real-Time Pavement Profile Sensing System Using Air-Coupled Surface Wave", which claims priority to U.S. Provisional Application No. 61/434,522, filed Jan. 20, 2011, entitled, REAL-TIME PAVEMENT PROFILE SENSING SYSTEM (RPPSS) USING AIR-COUPLED SURFACE WAVE. The contents of these priority applications are incorporated herein by reference.

STATEMENT REGARDING FEDERALLY SPONSORED RESEARCH OR DEVELOPMENT

The research leading to this invention was carried out with U.S. Government support provided under a grant from the National Institute of Standards and Technology (NIST) Technology Innovation Program (TIP), Grant No. 70NANB9H9012. The U.S. Government has certain rights in the invention.

BACKGROUND OF THE INVENTION

Highway pavement is typically a layered structure consisting of surface courses, a base, and a sub-base all deposited on the sub-grade. Deterioration of pavement results not only from surface cracks and potholes due to tire friction, but also from de-bonding or stripping of sub-surface layers due to material aging. Sub-surface initialized defects often develop before surface cracks are visible and lead to surface damage. According to the American Society of Civil Engineers (ASCE) Infrastructure Report Card in 2009, United States bridges received a grade "C" and roads received a grade "D-". Therefore, early detection and repair of the hidden sub-surface defects is of great importance in maintaining roadways.

Methods have been developed and utilized for sub-surface sensing, including Impact Echo (IE), Impulse Response (IR), Ground Penetrating Radar (GPR), Chain-drag, and Spectral Analysis of Surface Waves (SASW). IE is able to identify the de-bonding and properties of a shallow top layer. IR can test the overall dynamic stiffness/mobility of the entire pavement structure. GPR is best for locating metal materials, such as reinforcement rebar. Chain-drag can be used to find de-bonded areas through detecting the resulting hollow sound. SASW and its related methods are very popular for the ability to estimate the depth and elastic modulus of sub-surface layers.

Since first proposed in the 1980's, SASW has been widely applied in geology field tests for estimating the underground soil profile without coring or opening the ground. It utilizes the dispersion features of the surface wave that propagates horizontally in the soil when subject to an impact load. The dispersion curve represents the relationship between the wave speed, and wavelength or frequency. Once the dispersion curve is obtained from the test data, the layer profile and shear velocities can be estimated by inverting algorithms.

Efforts have been made to improve the accuracy and efficiency of SASW. For example, a stiffness matrices method was developed to perform inversion analysis to investigate pavement systems and concrete structures. Other methods based on the SASW principal have been developed, including the Multichannel Analysis of Surface Wave (MASW) method in which multiple sensors to record the complete wave field and resolve the different wave modes.

One major issue that negatively impacts the efficiency of the prior SASW methods is the iterative inversion process, which is typically time consuming and requires human expertise to set the initial and adjusted values of the elastic modulus profile. Consequently, these prior SASW methods are limited to being point-to-point, posted-processed stationary tests. Research is being done towards identifying faster and/or automated inversion analysis algorithms to enhance efficiency. One such algorithm constructs the dispersion curve through fitting a complex-valued curve to the phase information of the cross power spectra using a coherence function as a weighting function. In another, a Monte Carlo algorithm and maximum likelihood method were chosen to examine the possible solutions with minimal constraints and to estimate the uncertainties of the resulting model parameters. In order to identify the predominant propagation modes easily, an inversion method based on the maximum vertical flexibility coefficient was introduced. In addition, an algorithm called the peak-trough and frequency-wave number (PT/FW) technique was developed to determine the phase velocity more effectively as compared to the traditional phase difference method. Moreover, Genetic Algorithm (GA)-based inversion and combination of genetic and linearized algorithms in a two-step joint inversion have also been employed in recent years.

However, all of these improvements only modified the method of initializing and adjusting the assumed profile for quick convergence. The inversion still relies on the basic procedure of guessing first and then checking with forward analysis. A fast inversion algorithm named fast simulated annealing (FSA) global search algorithm minimizes the difference between the measured phase-velocity spectrum and the spectrum calculated from a theoretical layer model, including the field setup geometry. However, it is limited to resolving the properties of the first layer only.

BRIEF SUMMARY OF THE INVENTION

An innovative inversion algorithm is proposed for SASW processing, utilizing the fundamental features of the surface wave. Particle displacement distribution characteristics along the penetrating depth were found to dominate the relationship between shear velocity profile and the dispersion curve. The phase velocity at a certain wavelength (or frequency) is therefore expressed as a weighted combination of shear velocities within the penetrating depth using normalized particle displacements as weighting factors. A fast inversion algorithm is then established on the basis of this relationship. This new algorithm requires no manual input or adjustment of trial profiles, and therefore is fully automated. Since no forward analysis to the stiffness matrix is needed, either, this method is extremely fast.

An integrated mobile acoustic sensing system implementing this algorithm is also disclosed for use in estimating the profile and elastic modulus of pavement layers at a walking speed. An electrical hammer is applied to produce impact force to the ground. A microphone array is used to collect a portion of the leaky surface wave. A multi-channel data acquisition (DAQ) module collects and processes data along with a laptop computer. The inversion process is conducted with the fast inversion algorithm, which links a dispersion curve with shear velocities directly in relation to the attenuation of particle velocity.

BRIEF DESCRIPTION OF THE SEVERAL VIEWS OF THE DRAWINGS

The foregoing and other objects, features, and advantages of the invention will be apparent from the following description of embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
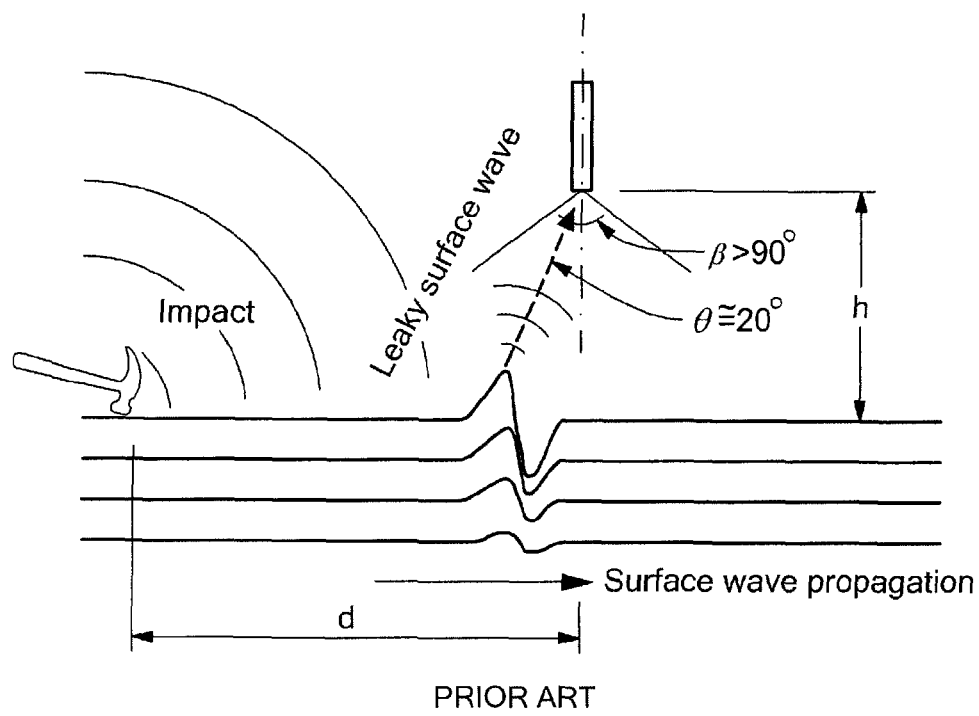
FIG. 1 illustrates the propagation of a leaky surface wave.

With regard to a layered pavement structure subject to a point load impact at the surface thereof, a surface wave propagates horizontally in addition to the propagation of P waves (compressional waves) and S waves (shear waves). This is depicted in FIG. 1. Surface vibration resulting from the surface wave propagation acts as an acoustic source and radiates an acoustic wave into the air close to the surface. This radiated acoustic wave is the so-called leaky surface wave. According to Snell's law, the leaky angle θ (relative to the surface normal) is determined by:

$$\sin(\theta) = \frac{C_a}{C_R} \quad (1)$$

where, $C_a$ is the acoustic wave velocity in the air and $C_R$ is the surface wave (Rayleigh wave) velocity in the pavement. $C_a$ is about 340 m/s, and $C_R$ can be 1000 m/s. Therefore, the leaky angle θ≅20°. The leaky surface wave can be detected with a directional microphone 10, which usually has an effective angle of approximately 100°.

Figure 2:
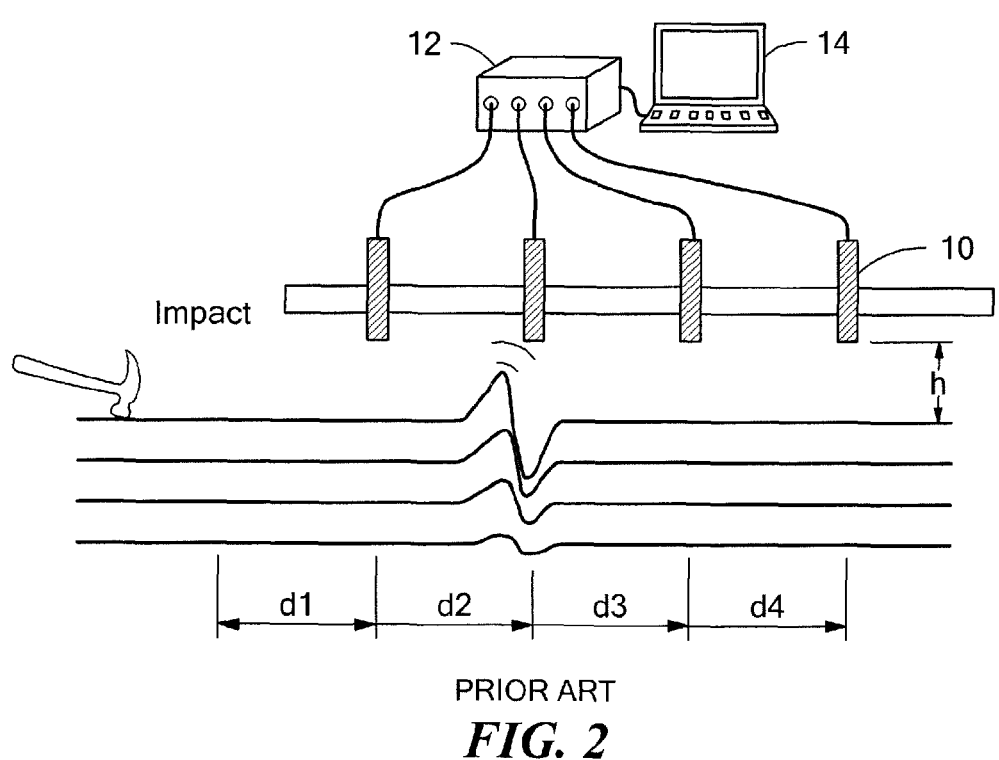
FIG. 2 illustrates a typical air-coupled SASW or MASW configuration.

The SASW test has typically been performed using accelerometers applied directly to the pavement surface for detecting the surface wave itself. More recently, the SASW test has been performed with microphones detecting the leaky surface wave. FIG. 2 shows a schematic configuration of directional microphones 10, a data acquisition (DAQ) device 12, and a computer processor 14, such as a laptop computer, used to carry out an air-coupled SASW test. Two or more microphones (four are illustrated) are placed a small distance h above the ground and connected to the DAQ and computer. When an impact force is applied, the detected acoustic signal contains both the leaky surface wave and the direct acoustic wave from the impact device, such as a hammer. When the microphones are near the pavement surface and the shear velocity of the pavement is much larger than that of the air acoustic velocity, the direct acoustic wave from the impact device arrives at each microphone later than the leaky surface wave. The difference in the arrival time can be calculated as:

$$\Delta t = \frac{\sqrt{d^2+h^2}}{C_a} - \frac{d}{C_R} - \sqrt{\frac{1}{C_a^2} - \frac{1}{C_R^2}} \quad (2)$$

At a typical configuration with d=0.5 m and h=0.05 m, this time lag can be on the order of 1 ms. Therefore, the leaky surface wave can be subtracted from the total signal by applying an appropriate time window on the acoustic data, a technique known as temporal windowing.

The air coupled-SASW strategy can be extended to air-coupled MASW by deploying an array of microphones 10 above the surface, as shown in FIG. 2. However, for ease of explanation, two microphones (SASW) are used in the presently disclosed data analysis.

As discussed above, the leaky surface wave can be extracted from the raw acoustic signals by windowing techniques. Forward dispersion analysis methods for traditional SASW can be used to analyze the leaky surface wave. However, known inversion analysis techniques for surface wave-based methods (SASW, MASW, and air-coupled SASW) are time consuming and require human expertise to set the initial and adjusted values of the elastic modulus profile.

According to the presently disclosed innovative technique, the attenuation curve derived from half-space structure is used as an approximation of particle displacement, the phase velocity is written as a weighted combination of shear velocity of the layers within the penetrating depth at the corresponding wavelength (or frequency). Based on this relationship, a fast automatic iterative inversion algorithm is developed; the inversion can give results nearly instantly.

When a half-space structure is subjected to a point force on the surface, three types of stress waves are generated: P-wave (compressional wave), S-wave (shear wave) and R-wave (surface or Rayleigh wave). Both body waves (P-wave and S-wave) propagate inside the structure but in perpendicular directions. The P-wave travels in the same direction with the particle vibration while the S-wave travels transversally. The R-wave, on the other hand, travels along the free surface of the structure. Due to material damping, all three waves attenuate as they propagate, though at different rates. At the surface, the amplitude of both P-wave and S-wave attenuate on the order of $r^{-2}$ (r is the radius from the source), while the surface wave attenuates much slower, on the order of $r^{-1/2}$.

The relationship between the velocities of stress waves can be expressed with linear expressions as:

$$\frac{V_S}{V_P} = \sqrt{\frac{1-2\upsilon}{2(1-\upsilon)}} \quad (3)$$

$$\frac{V_R}{V_S} \approx \frac{0.87 + 1.12\upsilon}{1+\upsilon} \quad (4)$$

where $V_P$, $V_S$, $V_R$ are velocities of the P-wave, S-wave and R-wave, respectively, and $\upsilon$ is Poisson's ratio.

Another basic feature of a surface wave is the shape of the wave-front. It has been discovered that the R-wave propagates radially outward along a cylindrical wave front, while the P-wave and S-wave propagate along a hemispherical wave front. This means the surface wave within the penetrating depth propagates outward at the same velocity.

On the other hand, the particle motion of a surface wave varies along the penetrating depth and finally fades out at the depth of approximately triple the wavelength. The approximate solution to the particle displacement of a surface wave along the penetrating depth is known to be, for Poisson's ratio $\upsilon$=0.5:

$$\begin{cases} u(y) = \left(-0.1298\, e^{-\frac{2\pi y}{Lc}} + 0.0706\, e^{-\frac{(0.2988)2\pi y}{Lc}}\right)\frac{P}{\mu} \\ v(y) = \left(0.1298\, e^{-\frac{2\pi y}{Lc}} - 0.2387\, e^{-\frac{(0.2988)2\pi y}{Lc}}\right)\frac{P}{\mu} \end{cases} \quad (5)$$

Figure 3:
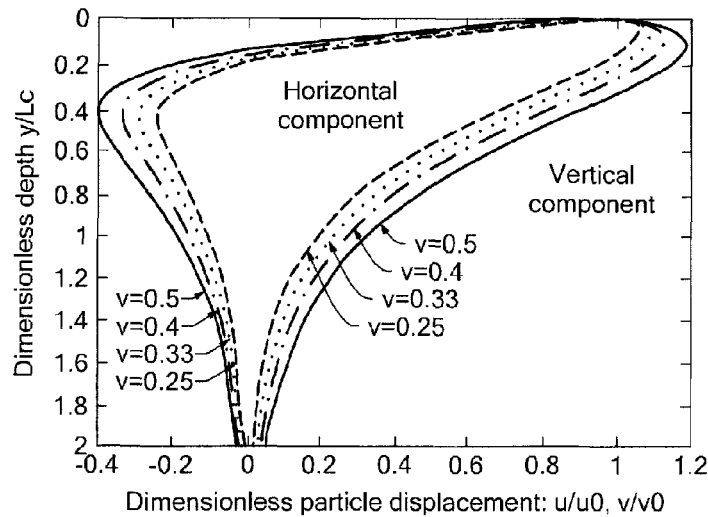
FIG. 3 graphically illustrates the distribution of particle displacement along penetrating depth of a surface wave.

And, for Poisson's ratio $\upsilon$=0.25: $-2\pi y/Lc$ $$\begin{cases} u(y) = \left(-0.2958\, e^{-\frac{(0.8474)2\pi y}{Lc}} + 0.1707\, e^{-\frac{(0.3938)2\pi y}{Lc}}\right)\frac{P}{\mu} \\ v(y) = \left(0.2507\, e^{-\frac{(0.8474)2\pi y}{Lc}} - 0.4341\, e^{-\frac{(0.3938)2\pi y}{Lc}}\right)\frac{P}{\mu} \end{cases} \quad (6)$$

where u and v are the horizontal and vertical components of the amplitude of particle displacement, respectively; $L_c$ is the wavelength; y is the depth; $y/L_c$ is the dimensionless depth; $\mu$ is the Lamé coefficient (shear modulus); and P is the impact force. When replacing u and v with the dimensionless displacement as $u/u_0$ and $v/v_0$, respectively ($u_0$ and $v_0$ are the displacement at the surface), the distribution of particle displacement amplitude can be plotted in a graph of the dimensionless displacement versus dimensionless depth, as shown in FIG. 3. The results for $\upsilon$=0.33 and $\upsilon$=0.4 in FIG. 3 are approximated by the linear interpolation between $\upsilon$=0.25 and $\upsilon$=0.5.

In an embodiment, an operator inputs a value of Poisson's ratio using an operator's interface. The input value is then provided to the data processor. The operator-input value is based upon at least one pavement material believed to be present in the pavement to be characterized.

Figure 4:
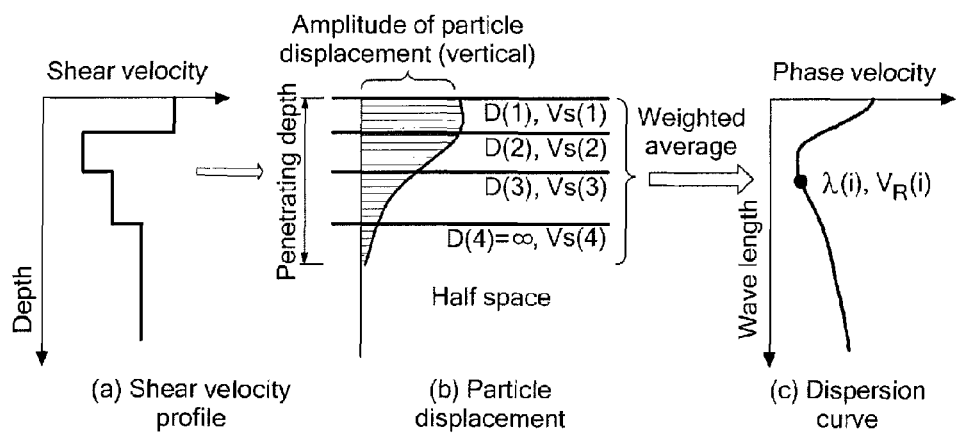
FIG. 4 illustrates the relationship between shear velocity profile and dispersion curve for a layered system, per the presently disclosed invention.

For a layered ground system, the propagation of a surface wave should remain in quasi-cylindrical wave front if the multimode effects are omitted. Therefore, one can conclude that a similar linear relationship exists between the phase velocity and the shear velocities of the underground layers. Since the wave in the penetrated layers travels at the same speed, it is apparent that an average of the shear velocities of these layers dominates the phase velocity. Prior research by others discovered that, compared with P-wave velocity, density and layer thickness, the shear wave velocity is the dominant parameter influencing changes in Rayleigh-wave phase velocity in the high-frequency range (>5 Hz). Moreover, from the viewpoint of energy conservation, the particle vibrating with a larger displacement must contribute more to the velocity of the entire surface wave. Therefore, the distribution of particle displacement along penetrating depth is chosen as a weighting factor in calculating the average. Since only the vertical motion component of the surface wave is measured by SASW (and MASW) sensors, only the vertical component of particle displacement contributes to the weighting factors. Thus, a weighted averaging relationship is proposed to connect the phase velocity and the layer shear velocities directly:

$$\begin{cases} V_R(\lambda) = \dfrac{\sum_{1}^{n} H'(i) V'_R(i)}{\sum_{1}^{n} H'(i)} & (7a) \\ H'(i) = \displaystyle\int_{y_{i-1}}^{y_i} v(y)\, dy & (7b) \\ V'_R(i) \approx \dfrac{0.87 + 1.12\upsilon(i)}{1+\upsilon(i)} V_S(i) & (7c) \end{cases}$$

where $V_R(\lambda)$ is the phase velocity of the surface wave as a function of wavelength $\lambda$; H'(i) is the equivalent thickness of layer i; $V'_R(\lambda)$ is the equivalent phase velocity at layer i; v(y) is the vertical component of the particle displacement at the depth y; $\upsilon$(i) is Poisson's ratio of layer i; and n is the total layers penetrated by the wavelength $\lambda$. Because v(y) attenuates fast along the depth, choosing $y_n=2\lambda$ is fairly accurate according to FIG. 3. Empirically, the total penetrating depth $y_n$ is about 0.3$\lambda$ to 0.4$\lambda$. FIG. 4 illustrates the graphic relationship expressed in equations (7a) to (7c).

Based on the above linear forward relationship between shear velocity profile and dispersion curve, a fast inversion algorithm is established to estimate the layer profile from the dispersion curve measured with SASW (and by extension with MSAW) tests. The algorithm consists of two stages: initializing and iterative adjusting.

Figure 5A:
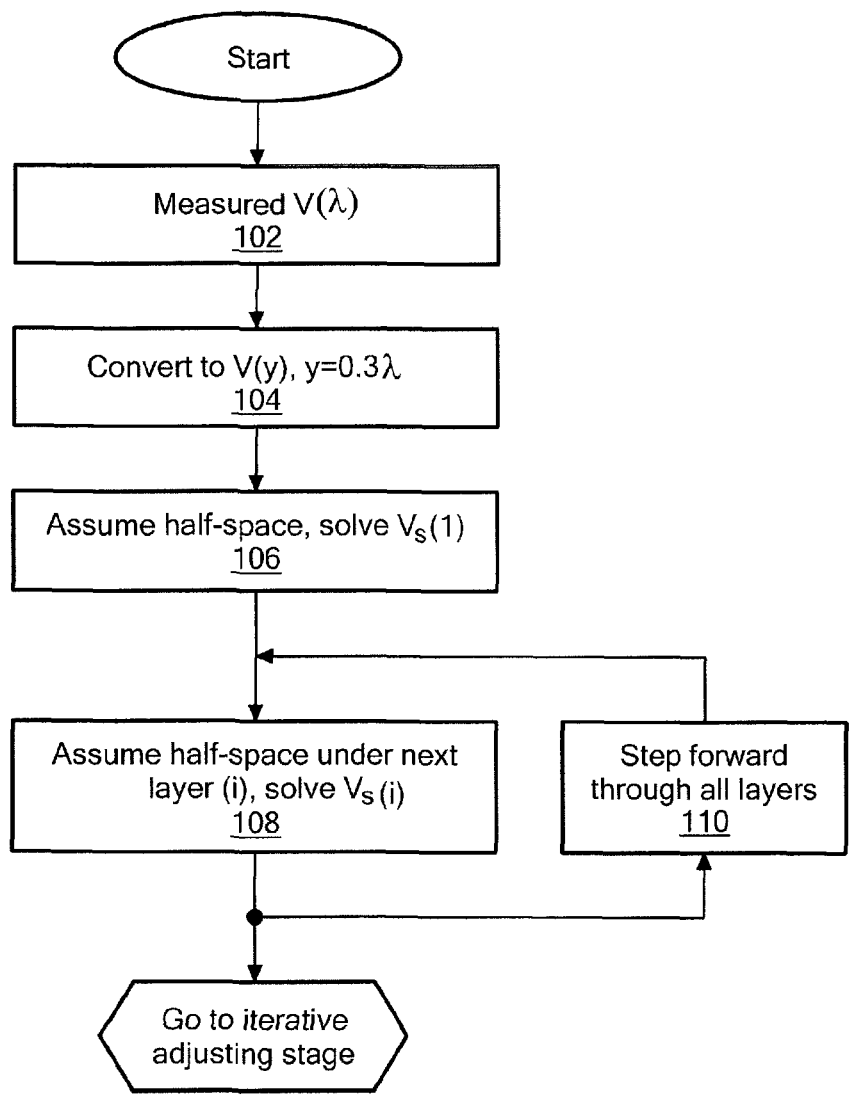
FIGS. 5A and 5B are flowcharts of an inversion analysis technique according to the presently disclosed invention.

With reference to FIG. 5A, the initializing stage starts from the top layer and assumes all the underneath layers are uniform half-space. The initial shear velocity of each layer can thus be solved from the above equations by stepping the layers forward.

Specifically, a dispersion curve, providing a function of phase velocity versus wavelength, is derived from the acoustically detected leaky surface wave according to established techniques 102. The dispersion curve data is converted to a discrete function of phase velocity versus approximate layer depth, using the empirical depth to wavelength ratio of 0.3 104 (though another ratio such as 0.4 could be used). Each such depth is assumed to be a layer. Starting from the first layer, assume the entire structure is a half-space, whereby the initial value for the shear velocity of the first layer $V_S^0(1)$ can be solved from the equations given above 106. For the second layer, assume that layer and everything below are a single half-space, and solve for the initial value of shear velocity for the second layer $V_S^0(2)$ 108. Repeat this process for all subsequent layers to achieve an initial shear velocity value for each 110.

Figure 5B:
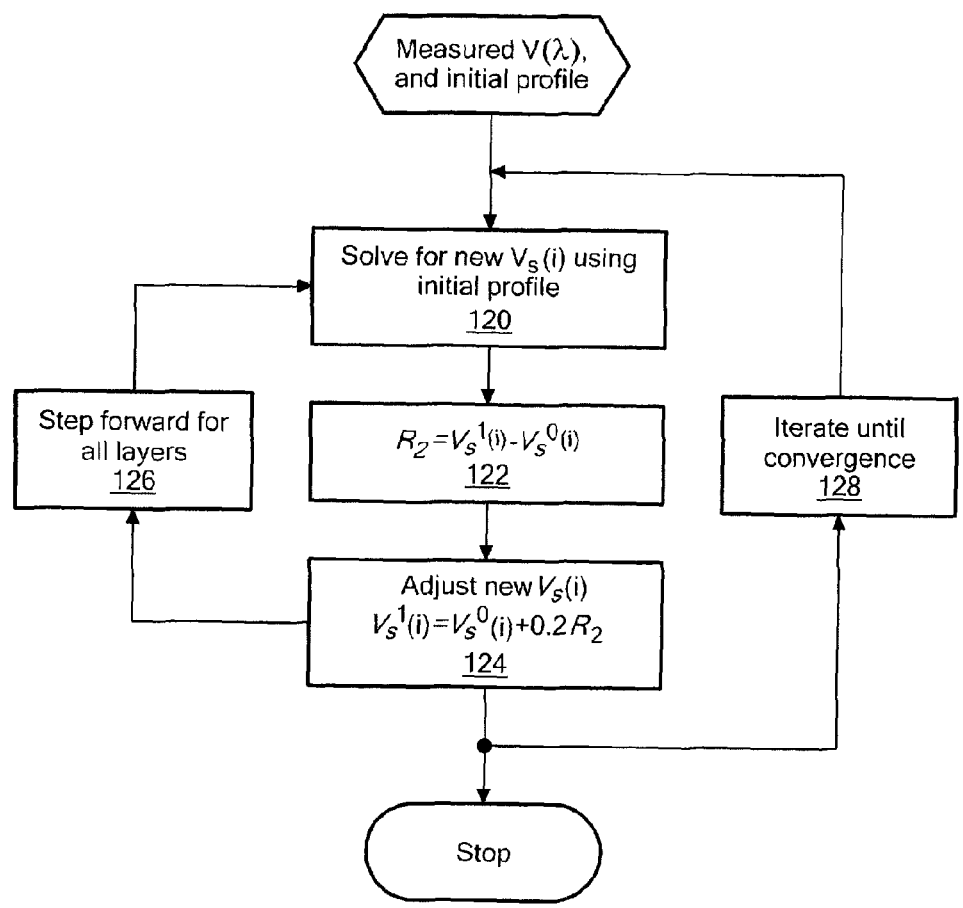

With reference to FIG. 5B, the iterative adjusting stage repeats the procedure of the initializing stage but replaces the half-space assumption with the initially determined shear velocities. The dispersion of the top-most material won't be affected by the properties of the lower layers since they are relatively remote from the top material. All lower layers are regarded as half-space relative to the top-most layer. Therefore, the shear velocity for the first layer represents a true solution for the shear velocity of that layer and no iteration is required. Consequently, the iterative adjusting stage begins with the second layer.

Starting with the second layer, the second layer shear velocity $V_S^1(2)$ is left unknown and is derived from the above equations using the previously obtained shear velocities of all other layers 120. This results in a new shear velocity value $V_S^1(2)$ for the second layer. A difference value $R_2$ for layer two is then calculated: $R_2 = V_S^1(2) - V_S^0(2)$ 122. In one embodiment, the shear velocity of the second layer $V_S^1(2)$ is adjusted by 20% of $R_2$ for better convergence: $V_S^1(2) = V_S^0(2) + 0.2R_2$ 124. The exact adjustment percentage may be more or less than 20% and may be empirically established for a given pavement section under analysis. Next, one steps forward and solves for new values for all subsequent layers 126. These steps are repeated across the layers until a predetermined degree of convergence is achieved 128.

Because in each step of the inversion a discrete point is regarded as a small layer, the inversion method does not determine actual layers and depths directly. Instead, the actual layers and depths are observed from the inverted shear velocity profile. As long as the inversion is correct, the small layers comprising an actual layer should have very similar shear velocities in the inverted profile. While conventional inversion methods are sensitive to a prior assumed initial shear velocity profile, often leading to multiple valid solutions, the presently disclosed technique requires no assumed layer depth profile. The present inversion algorithm thus involves no human expertise.

It can be seen from the above description and FIGS. 5A and 5B that all calculations in the inversion are purely algebraic operations for a given discrete dispersion curve; no differential equations are involved. Therefore, the entire inversion procedure is extremely fast and fully automated in comparison to the traditional inversion procedures.

Figure 6:
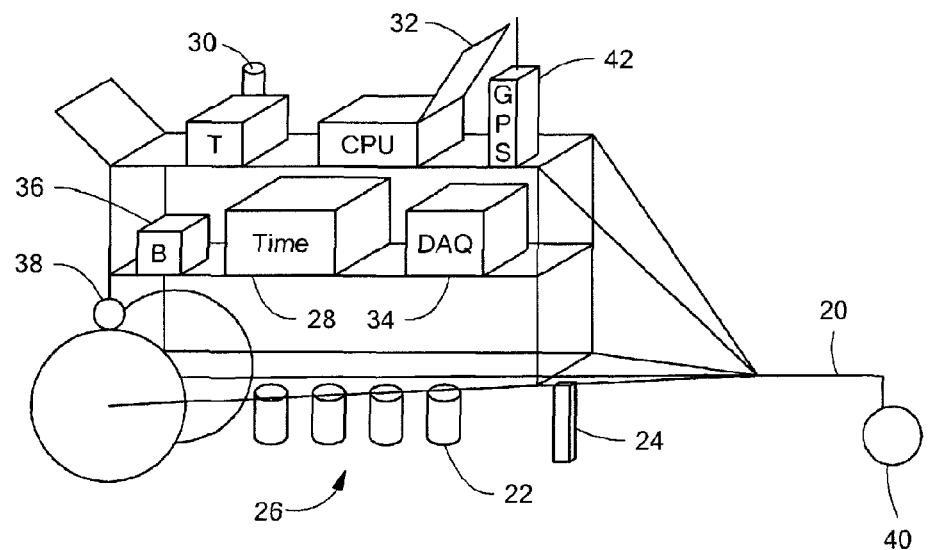
FIG. 6 is a schematic depiction of a Mobile Acoustic Sub-surface Sensing (MASS) system according to the presently disclosed invention.

A Mobile Acoustic Sub-surface Sensing (MASS) system, shown schematically in FIG. 6, provides a mobile platform for carrying out sub-surface analysis using the presently disclosed surface wave analysis technique. In a first embodiment, it utilizes a three-wheeled cart 20 with a triangular base. Other configurations are employable. An array 26 of microphones disposed within noise-canceling enclosures 22 is installed along the center line of the cart, pointing toward the ground, with 1 cm clearance therebetween. Each microphone of the array is protected within a sound enclosure 22 to isolate the microphone from direct noise from vibration caused by hammer 24 impact. Greater detail for one embodiment of the noise-canceling enclosure is provided below.

In a first embodiment of the MASS system, the hammer is provided as an electrical hammer, consisting of two electro-magnetic (EM) coils, and is mounted in line in front of the microphone array. Greater detail for one embodiment of the hammer is provided below. An accelerometer is mounted on the top of the hammer core to measure the hammer response and to trigger a recording signal as well.

A time controller unit 28 is deployed to adjust the time delay between hammer coils. An operating handle or trigger 30 ("T") is designed to actuate the strike by driving the hammer down against the pavement surface. A laptop 32 ("CPU") is used to control the whole system and to perform the surface wave analysis. A DAQ device 34 ("DAQ") is provided to receive and store data from the microphone array 26. In a first embodiment, the maximum sampling rate of the DAQ is set to 200 KHz for all 12 available channels. A global positioning system (GPS) receiver 42 ("GPS") may be integrated into the system to geographically localize the test data associated with each hammer strike.

Preferably, a pyramidal sound absorbing foam liner (not shown) is attached under a lower equipment shelf to absorb sound reflections. Battery power 36 ("B"), such as provided by a pair of 12-volt batteries, provides power to the system. An odometer 38 is installed at one of the rear wheels or rear axle (not shown) to record the travelling distance. In addition, a small swivel wheel (or wheels) 40 is used at the front of the cart. One skilled in the art will recognize that variations in the configuration of the cart and the placement of its components may be utilized.

In alternative embodiments, more than one array of microphones is employed. For example, three such arrays of microphones, each comprised of four linearly disposed microphones, can be employed. The arrays may be completely discrete or may share one or more microphones. One specific example would be to dispose three such arrays along the bottom of the cart shown in FIG. 6. Instead of just the axially aligned array 26 as shown, two additional arrays can be provided on either side of the illustrated array, forming a V-shape therebetween. In a further embodiment, all three arrays can share one forward-most microphone. The inter-microphone spacing need not be the same for all arrays.

An integrated analysis program is developed using a technical computing language such as MATLAB (The Mathworks Inc.) using the methods described herein. After the detected acoustic data is transferred from the DAQ to the laptop (or other computing device), the program run by the laptop automatically locates the hammer excited data out of the continuous signal stream and extracts the leaky surface wave by applying an appropriate temporal windowing function. Dispersion and automatic iterative inversion, as described above, are executed by the laptop to define the estimation of profiles of sub-surface shear wave velocity and elastic modulus. Owing to the disclosed fast inversion algorithm, all these analyses are finished rapidly (about 1 s given processing speeds commonly found in current laptop computers) if the graphic output of intermediate results, such as time history, coherence and dispersion curve, are omitted. In a further embodiment, the disclosed algorithm is implemented in a C language program and embedded into the computing device for efficient real-time implementation.

To supply broadband transient impact on the pavement, an electromagnetic hammer unit 24 is assembled from two coaxially disposed linear solenoids (for example, 40 pound solenoids manufactured by Amenity). One solenoid acts to lift a hammer core while the other acts to shoot or drive the core downward. The hammer unit is controlled with two time delay relay units (for example, Magnecraft/Schneider Electric part number 528-TDRSOXP-24V). Power is shifted from the lift solenoid on the top to the shoot solenoid on the bottom. In this case, the hammer core is lifted to the optimal position ready to be shot down with large impact force. The impact duration is controlled with the time delay relay. The core position and triggering is controlled with the operating handle 30, described in further detail below.

To acquire the impact-echo data with the air-coupled SASW test, a shock accelerometer is attached to the top of an aluminum extension bar embedded coaxially within the magnetic steel hammer core. Data from the accelerometer is conveyed via a wired or wireless data channel to the DAQ and on to the computing device.

Additionally, the hammer tip is designed to be replaceable. Any one from a set of exchangeable tips, each having a unique shape and manufactured of similar or disparate materials, can be installed on the end of hammer core to provide different impact characteristics, thus allowing the hammer strike to be tuned to the respective pavement surface and sub-surface.

In an alternative embodiment, the impact source is a compressed air gun capable of firing a variety of projectiles of various geometries and materials, the selection of which depends at least in part upon the pavement to be profiled.

In an alternative embodiment, the impact results from a vehicle tire(s). In addition to exciting acoustic waves in air, tires excite elastic waves in the ground. Since each tire on a vehicle excites Rayleigh waves both forward and rearward, an appropriately designed array of directional microphones placed under the vehicle can be used to extract estimates of surface wave dispersion with sufficient accuracy to assess subsurface damage. To generate a detectable surface wave, factors such as geometry, materials, stiffness, mass, etc. may be taken into consideration in designing a tire acting as an impact source. External elements can also be applied to the exterior, rolling surface of the tire to achieve this goal. Much in the way chains are mounted on tires for traction in winter conditions, one or more road impacting elements, such as one or more large metal studs or metal bars may be attached to the tire rolling surface.

In yet another embodiment, a weight or other mass is affixed to the inside surface of the tire. As the tire rolls across the surface to be characterized, the weight periodically impacts the surface, through the tire itself, and imparts the desired impact, thus generating a Rayleigh wave in the pavement itself.

Figure 7:
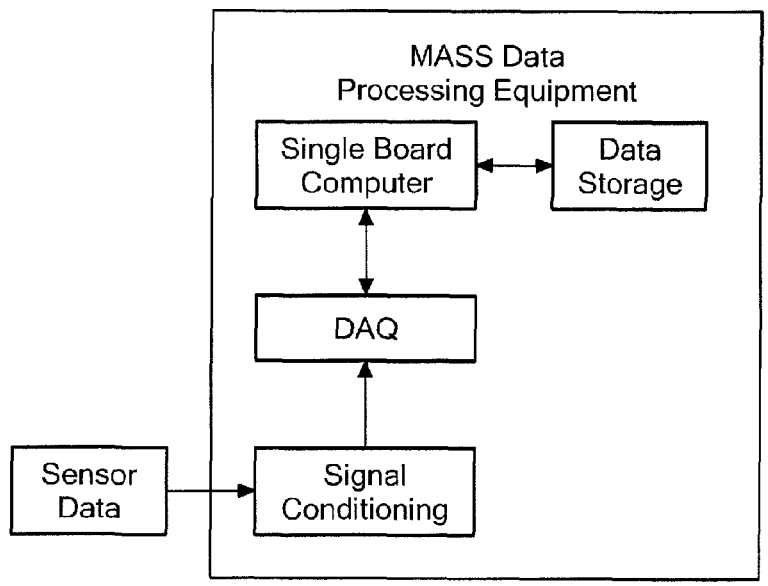
FIG. 7 is a block diagram of data processing equipment associated with the MASS system of FIG. 6.

FIG. 7 shows the MASS system data processing equipment system diagram without the power components. The data processing equipment that comprise the MASS system includes, in a first embodiment, a signal conditioner, a DAQ board, a computing device (in this embodiment, a Single Board Computer (SBC)), a DC power converter, a battery or batteries, and data storage such as a solid state hard drive. In one implementation, the signal conditioner is a Danforth Corporation Model SCM5B48 signal conditioner. The DAQ is implemented with a General Standards Corp. Model PC104P-24DSI12 12-channel analog input board which features low noise, 24-bit resolution, low phase distortion and multi-board synchronization. The computing device is provided as a VersaLogic Corporation Mamba EBX SBC featuring a high-performance Intel Core 2 Duo processor. QNX is selected as the Operation System in this exemplary embodiment.

The working height of the hammer 24 core is adjusted with a operating handle, such as the TCI Automotive Model 748000 shifter. When the MASS cart is moving between impact points, the EM hammer is lifted to a higher elevation to protect the hammer unit from accidentally impacting the underlying pavement. The drive solenoid power is selected as the data acquisition trigger to initiate the data record.

Figure 8:
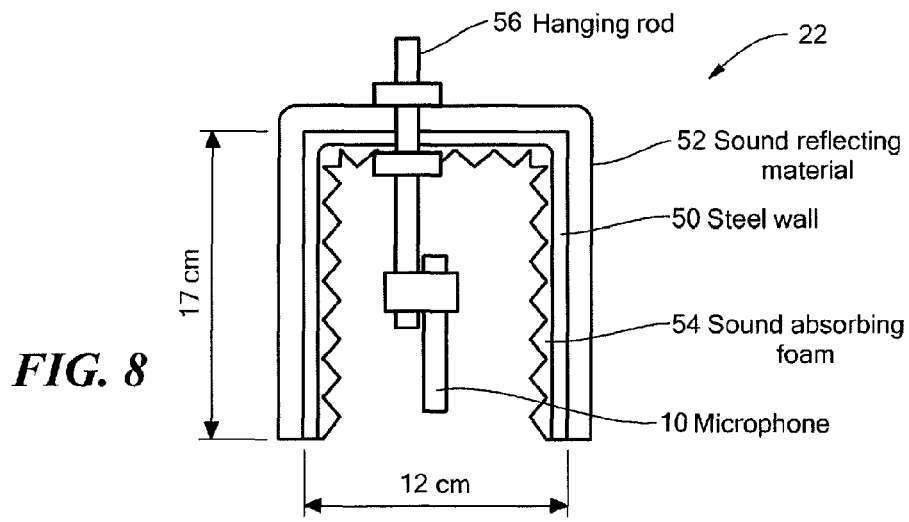
FIG. 8 is a section view of a noise canceling enclosure for a directional microphone as employed in the MASS system of FIG. 6.

In order to improve the signal to noise ratio and subsequently increase the coherence between microphones, a noise-canceling enclosure 22 is designed to block the direct noise from the hammer vibration. FIG. 8 illustrates a first embodiment of such a noise-canceling enclosure. A cylindrical steel enclosure 50 having a closed end and an open end is used as the base structure. A sound reflecting material with dense skin 52 wraps over the external surface of steel enclosure to reduce the penetration of outside noise. A pyramidal, sound absorbing foam liner 54 is fitted on the internal surface of the cylindrical wall, on the closed end of the enclosure, or both, to absorb inside acoustic reflection. A directional microphone 10 is mounted in the center of the cylinder, suspended from a hanging rod 56 attached to the closed end of the enclosure, with 1 cm vertical distance from the open end of the enclosure. Vibration absorbing materials such as rubber gaskets are preferably used to attach the microphone to the hanging rod and to mount the hanging rod to the enclosure for the purpose of further isolating the microphone from physical vibrations. Suitable dimensions for the enclosure 22 are shown in FIG. 8, though other dimensions are employable.

Figure 9A:
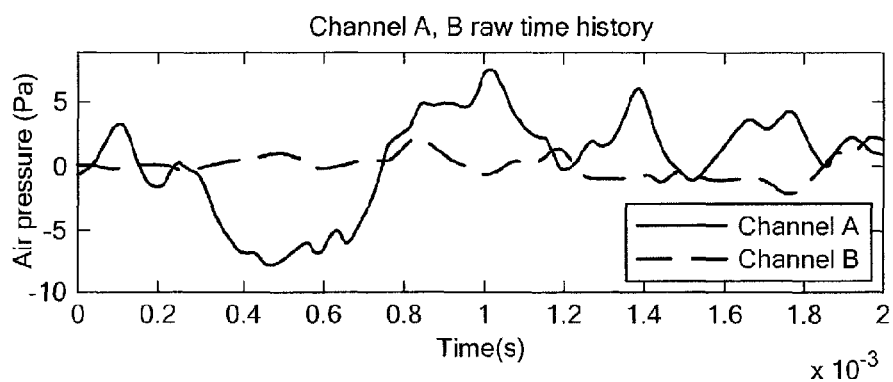
FIGS. 9A and 9B are graphs comparing directional microphone data with and without the use of the noise canceling enclosure of FIG. 8.
Figure 9B:
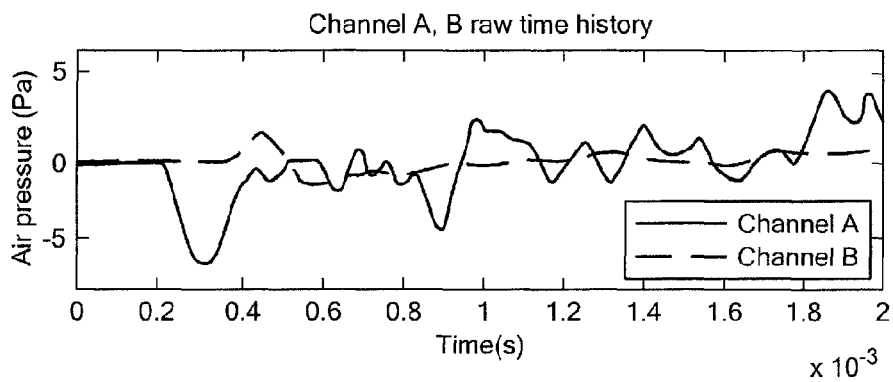

FIGS. 9A and 9B demonstrate the beneficial effect of employing such a noise-canceling enclosure 22. Without the enclosure (FIG. 9A), the noise level is so high that the leaky surface wave can hardly be separated from the noise in time domain. This is particularly true for Channel B, for which almost no leaky surface wave can be identified. After the enclosure is applied to the microphone array (FIG. 9B), the leaky surface wave can be easily identified and separated over the entire time history. In addition, the signal received before the leaky surface wave arrives at the enclosed microphones is beneficially flat and near zero.

For validation purposes, mobile tests were performed using the MASS hardware and software system in an asphalt parking lot and on a concrete lab floor. In the parking lot, test locations were marked by a chalk stick 60 cm apart. The microphone array was 1 cm above the ground with 20 cm spacing between each of the four microphones. The cart moved along the chalk marks and the hammer shot at the marked points. Five shots were applied at each location. The sampling rate was set to 200 KHz for all sensors. The entire system was handled by one person, including pushing the cart and operating the test control. On the concrete lab floor, eight hammer strikes were applied at two adjacent locations 1 m apart.

Figure 10A:
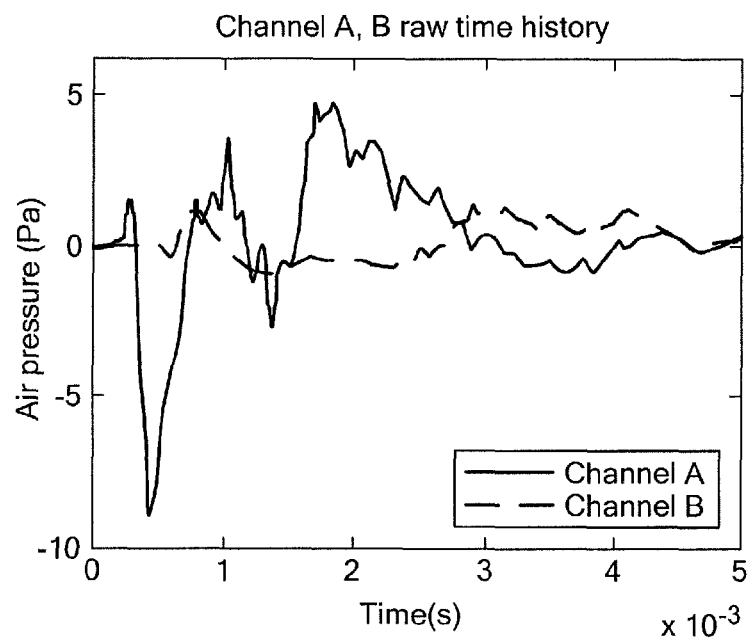
FIGS. 10A and 10B are graphs of raw and temporally windowed microphone data for use in the MASS system of FIG. 6.
Figure 10B:
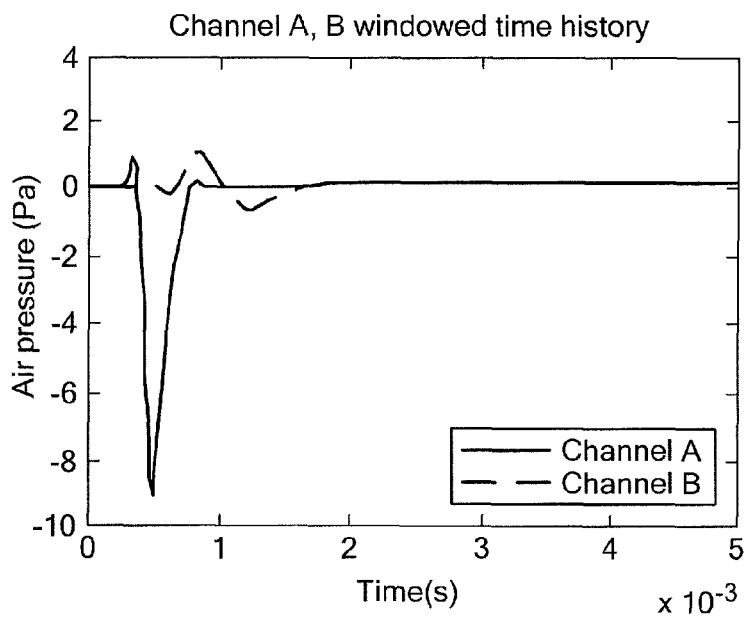

FIGS. 10A and 10B illustrate the time history of one hammer strike in the parking lot. The surface waves at two microphones 40 cm apart are extracted by applying a Hanning window on the raw data. The window size of the first channel is chosen to be twice the time length of the minimum peak value. The window size of the second channel is chosen to be the size of the window of the first channel plus the acoustic travel time of hammer noise between two channels. It can be observed from FIG. 10B that the extracted surface wave is fairly smooth and represents the raw data appropriately.

Figure 11A:
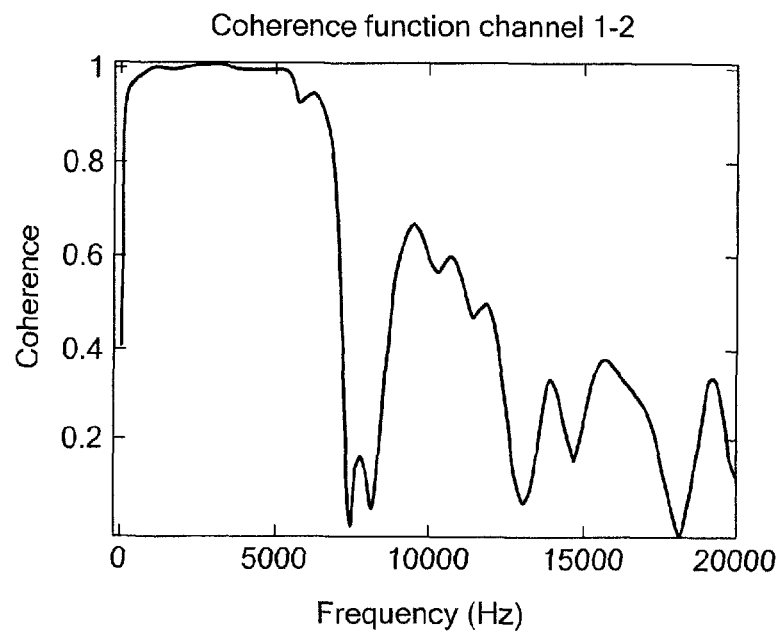
FIGS. 11A and 11B are graphs of a coherence function and dispersion curve for a test of the MASS system of FIG. 6.
Figure 11B:
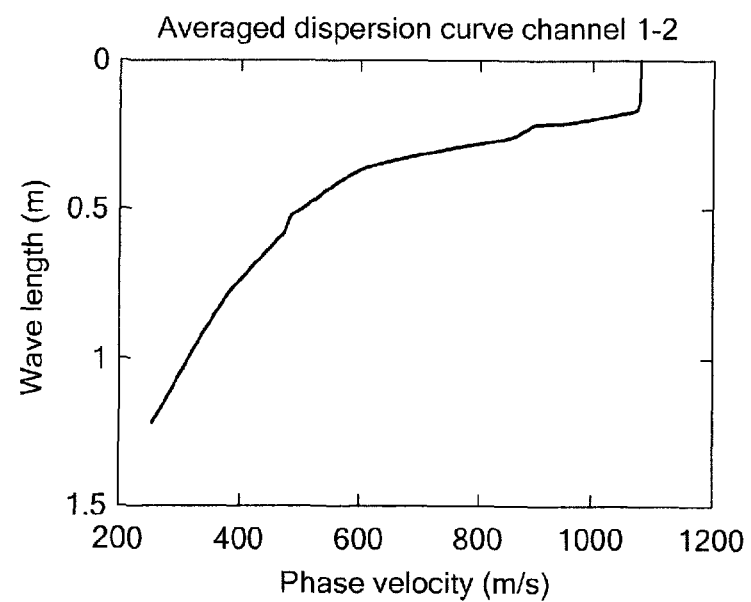

FIGS. 11A and 11B show the coherence and dispersion curve of the selected channels. It can be seen from FIG. 11A that the two channels share very good coherence from about 200 Hz up to 7000 Hz. The effective dispersion curve is calculated for this frequency band and plotted in FIG. 11B. For the inversion algorithm to run automatically, the dispersion curve has to start from the surface (depth zero). The phase velocity at the unidentified shallower depth (frequency above 7000 Hz) is assumed to be same as the first identified depth. This assumption can be seen in abrupt vertical segment at the top of the dispersion curve in FIG. 11B.

Figure 12:
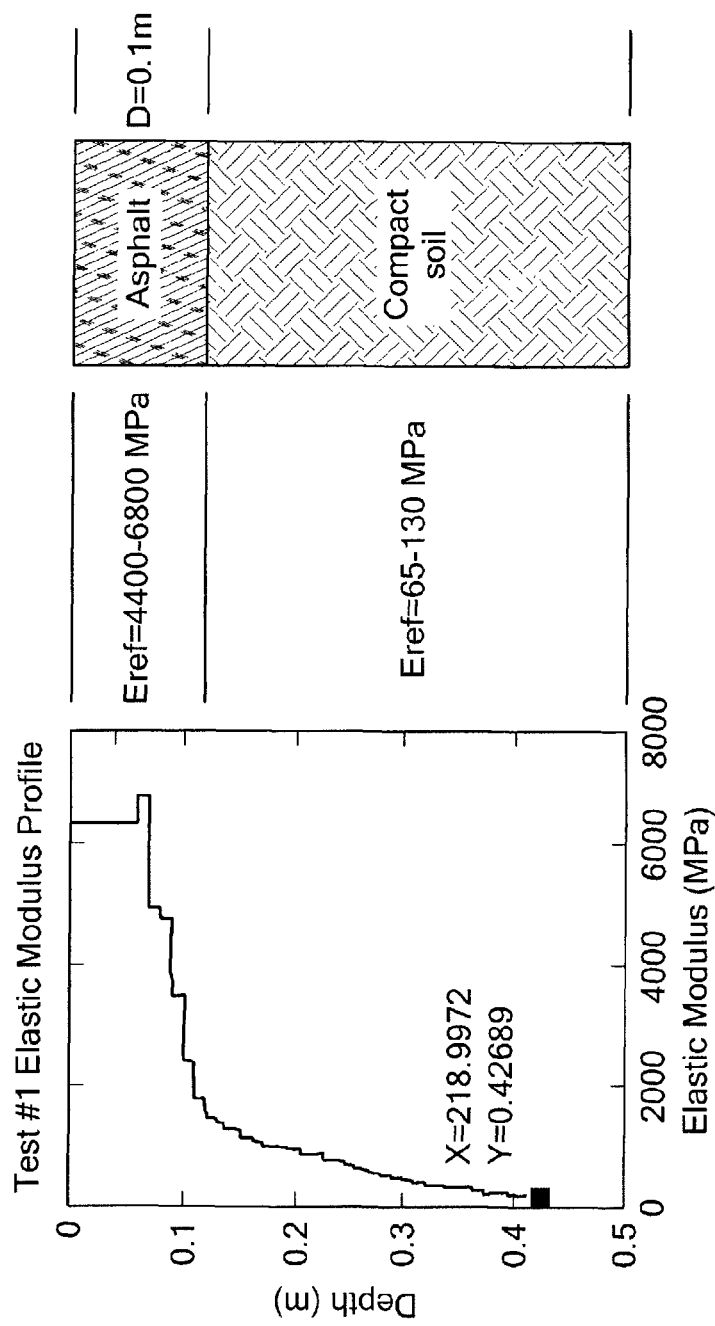
FIG. 12 graphically illustrates an estimated elastic modulus profile for the test of FIGS. 11A and 11B.

The final estimated profile of elastic modulus is presented in FIG. 12. Without further information about the subsurface material, uniform mass density of 1800 kg/m³ and Poisson's ratio of 0.3 were assumed in the calculation of elastic modulus. According to the profile, the first asphalt layer has an estimated depth of 0.1 m and estimated elastic modulus of 6400 MPa, which falls into the range of a regular asphalt concrete material known to have an elastic modulus of 4400 MPa to 6800 MPa.

Figure 13A:
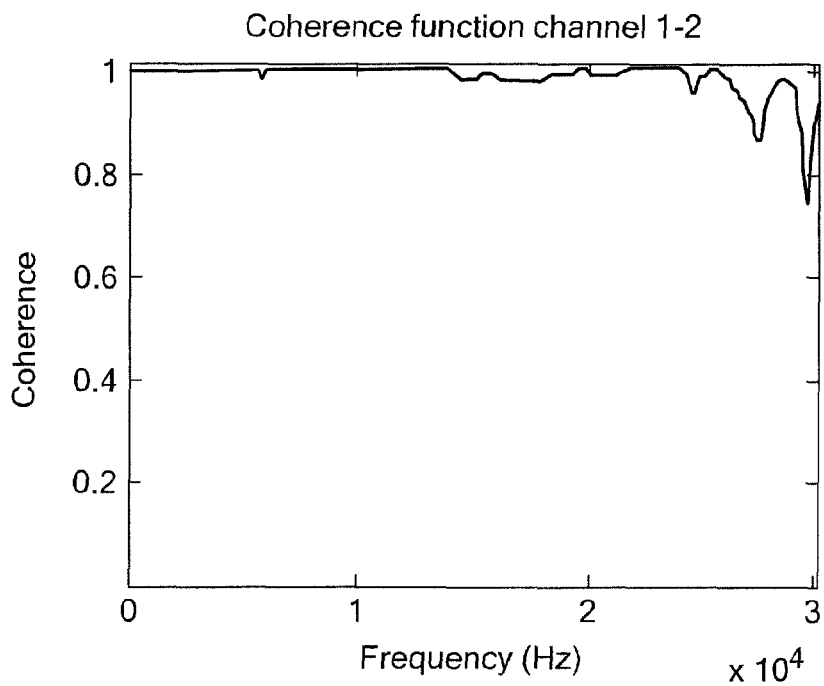
FIGS. 13A and 13B are graphs of a coherence function and dispersion curve for a second test of the MASS system of FIG. 6.
Figure 13B:
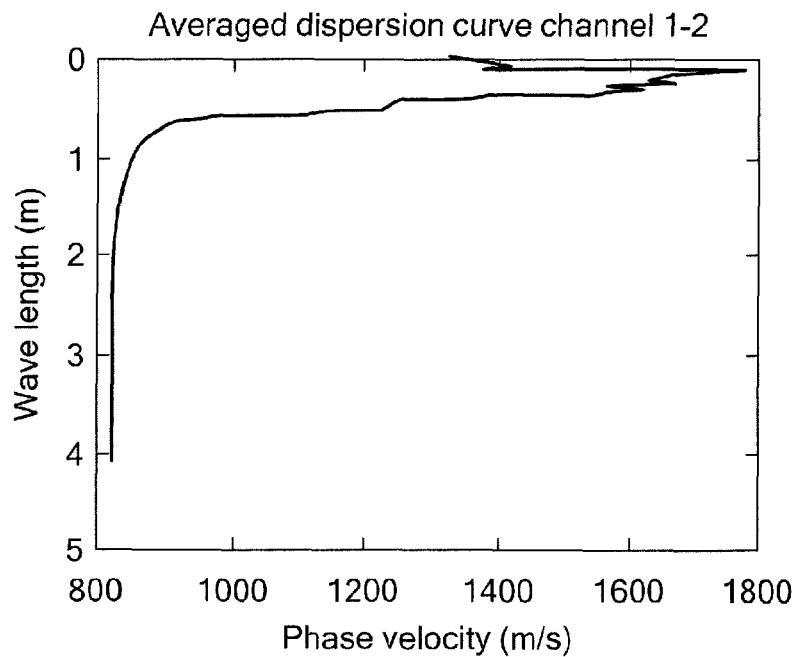

The same windowing and dispersion analysis strategy was applied in the analysis of the concrete lab floor test. The extracted surface wave from the microphone data shows very good coherence up to 30 KHz, as shown in the FIG. 13A. The significant improvement of the coherence may be attributed to the much stronger material of the lab floor. This can be seen in FIG. 13B where the calculated dispersion curve starts almost from the very top of the surface to the wavelength of 4 m.

Figure 14:
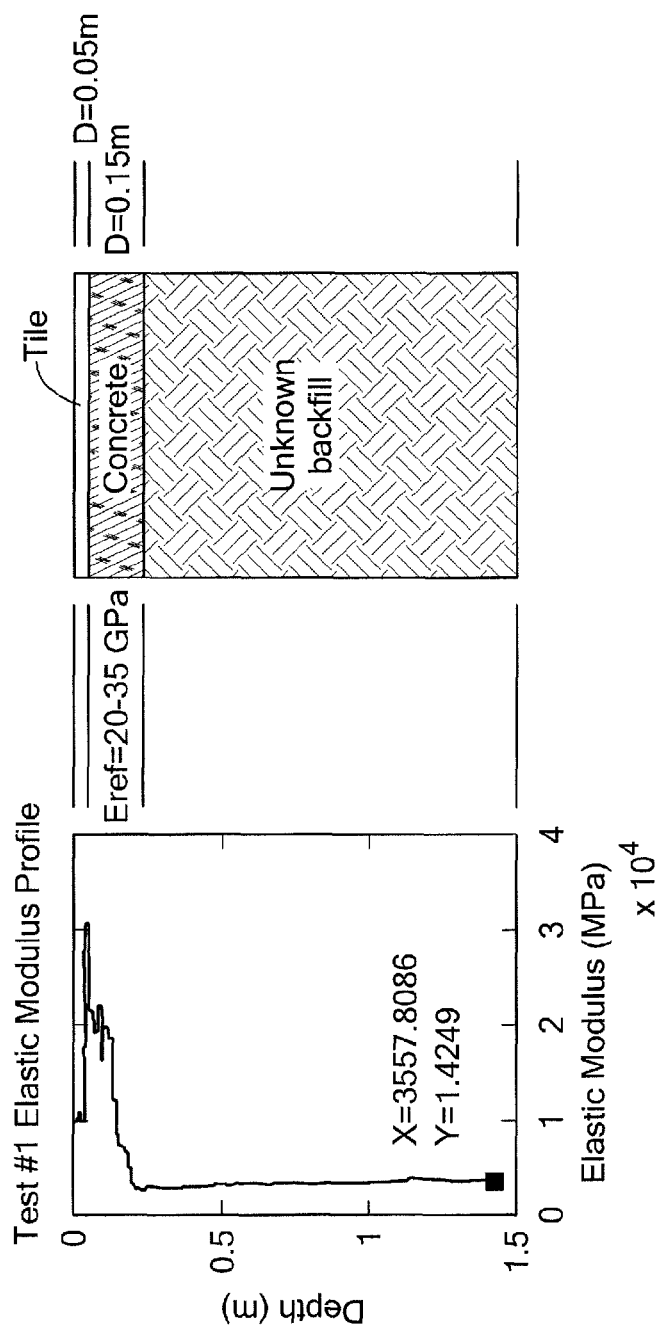
FIG. 14 graphically illustrates an estimated elastic modulus profile for the test of FIGS. 13A and 13B.

The estimated elastic modulus profile for the concrete lab floor is shown in FIG. 14. Two distinct layers above a half-space foundation are identified from the profile. The first 0.05 m thin layer with 10 GPa modulus is believed to be the material of surfacing tiles on the concrete floor. The concrete floor is estimated to be 0.15 m thick with modulus of roughly 20-25 GPa. Compared with the reference range 20-35 GPa for regular concrete materials, the estimated value is reasonable. The material under the concrete floor with estimated elastic modulus of 3.6 GPa is unknown.

Since the invention of surface wave based methods like SASW and MASW in 1980s, it has always been recommended to perform multiple tests at each location with various sensor spacings and even reverse sensor orientations. The strategy of performing post-test data averaging for these multiple tests was utilized to reduce noise and produce reliable estimation. However, with a moving test platform using microphones and producing nearly real-time output, the multiple strike technique is not preferred.

Due to the more recent development of improved sensor technology and the automatic hammer described in this paper, the repeatability of each test performance is much improved. Thus, the presently disclosed estimation of elastic profile at each location may be made from only one hammer strike.

Furthermore, hammer strikes that have good coherence usually give good estimation. Strikes with poor coherence are most likely caused by some error during impact processing, such as hitting at the boundary of the uneven dent of a previous impact. Averaging poor samples actually compromises, instead of improves, the estimation accuracy. Therefore, as long as good coherence is obtained, one hammer strike is acceptable for reliable estimation for the present mobile test strategy. The present system may be modified to detect poor coherence and alert an operator to the need to perform one or more additional tests.

In order to verify the above expectation, the repeatability of the MASS system was investigated. Table 1 shows the comparison of five consecutive strikes on the concrete lab floor. For the convenience of comparing, the elastic modulus of each layer was selected as the average/equivalent value in the thickness for each hammer strike. Then the average value, standard deviation and bias value were calculated for all five strikes. The comparison in the table shows the top layer has lowest repeatability with 46.3% bias in thickness and 23.9% bias in elastic modulus. The other two layers have very good repeatability with less than 10% bias in both thickness and elastic modulus estimation.

TABLE 1

| | | \multicolumn{8}{c}{Variation of estimated shear wave profile} | | | | | | | |
|---|---|---|---|---|---|---|---|---|---|
| Layer | | Strike 1 | Strike 2 | Strike 3 | Strike 4 | Strike 5 | Average | Deviation | Bias (%) |
| 1 | Thickness (m) | 0.039 | 0.026 | 0.03 | 0.069 | 0.039 | 0.041 | 0.019 | 46.3% |
| | E (GPa) | 10 | 8.32 | 13.03 | 6.92 | 10.9 | 9.83 | 2.35 | 23.9% |
| 2 | Thickness (m) | 0.157 | 0.157 | 0.148 | 0.126 | 0.157 | 0.149 | 0.0134 | 9% |
| | E (GPa) | 21 | 22.4 | 18.7 | 20.6 | 19.2 | 20.38 | 1.48 | 7.3% |
| 3 (half space) | Thickness (m) | 1.23 | 1.28 | 1.37 | 1.29 | 1.23 | 1.28 | 0.057 | 4.5% |
| | E (GPa) | 3.3 | 3.6 | 4.08 | 3.7 | 3.3 | 3.596 | 0.324 | 9% |

Many changes in the details, materials, and arrangement of parts and steps, herein described and illustrated, can be made by those skilled in the art in light of teachings contained hereinabove. Accordingly, it will be understood that the following claims are not to be limited to the embodiments disclosed herein and can include practices other than those specifically described, and are to be interpreted as broadly as allowed under the law.

What is claimed is:

1. A method for characterizing at least one layer of pavement to a predetermined penetrating depth, comprising:
   providing a data processor for receiving audio input signals;
   disposing an array of microphones proximate an upper surface of the pavement, the array being disposed on a wheeled platform and in communication with the data processor for communicating audio input signals thereto;
   applying a substantially vertical point load impact to the pavement;
   detecting with a plurality of microphones in the array a leaky surface wave generated by the impact;
   defining, by the data processor, a dispersion curve from the leaky surface wave, the dispersion curve mapping phase velocity versus wavelength or frequency; and
   calculating an inversion of the dispersion curve, by the processor, by
      starting at the lowest wavelength or highest frequency corresponding to the pavement surface, and repeating for each consecutive higher wavelength or lower frequency corresponding to a substantially horizontal layer along the predetermined penetrating depth, dividing the respective phase velocity value by a predetermined estimate of the amplitude of particle vertical displacement for the substantially horizontal layer, while assuming all deeper layers are uniform half-space, to derive estimates of shear velocity at corresponding penetrating depths, and iteratively adjusting the estimates of shear velocity by repeating, starting at the lowest wavelength or highest frequency and for each consecutive higher wavelength or lower frequency corresponding to each substantially horizontal layer along the predetermined penetrating depth, the steps of dividing the respective phase velocity value by a predetermined estimate of the amplitude of particle vertical displacement for the substantially horizontal layer, while taking into consideration the derived estimates of shear velocity value, until convergence; whereby the method is repeated at each of consecutive locations on the pavement as traversed by the wheeled platform.

2. The method of claim 1, wherein the step of defining the dispersion curve is performed within a frequency band across which a coherence curve, calculated by the data processor from the audio signals, has coherence values substantially equal to one.

3. The method of claim 1, further comprising the step of temporally windowing the received audio signals, by the data processor, to eliminate direct acoustic noise resulting from the impact.

4. The method of claim 1, further comprising the step of providing a sound barrier enclosure for each microphone of the array of microphones.

5. The method of claim 4, wherein the sound barrier enclosure comprises a substantially cylindrical enclosure having a first closed end, a second open end, and a cylindrical wall, the respective microphone being disposed within and coaxially with the substantially cylindrical enclosure.

6. The method of claim 5, wherein the exterior surface of at least one of the first closed end and the cylindrical wall is provided with a sound reflecting material.

7. The method of claim 5, wherein the interior surface of at least one of the first closed end and the cylindrical wall is provided with a sound absorbing material.

8. The method of claim 1, wherein the step of disposing an array of microphones comprises disposing an array of directional microphones, each having a respective acoustic axis substantially orthogonal to the pavement upper surface.

9. The method of claim 1, wherein the predetermined estimate of the amplitude of particle vertical displacement correlates dimensionless particle displacement with dimensionless depth, and is dependent upon a value for Poisson's ratio.

10. The method of claim 9, wherein a Poisson's ratio value is provided to the data processor by an operator using an operator interface based upon at least one pavement material believed to be present in the pavement to be characterized.

11. A system for characterizing at least one layer of pavement to a predetermined penetrating depth, comprising:
a data processor for receiving audio input signals;
an array of microphones proximate an upper surface of the pavement, the array being in communication with the data processor, for detecting a leaky surface wave in the pavement, and for communicating audio input signals in response to the detected leaky surface wave;
a substantially vertical point load impact subsystem for selectively imparting a point load impact onto the pavement surface and for generating the leaky surface wave in the pavement, and
a wheeled platform; wherein the data processor, the array of microphones, and the substantially vertical point load impact subsystem are disposed on the wheeled platform and the system can be transported on the pavement;
wherein the data processor is operative to define a dispersion curve from the leaky surface wave, the dispersion curve mapping phase velocity versus wavelength or frequency; and
wherein the data processor is further operative to calculate an inversion of the dispersion curve by,
starting at the lowest wavelength or highest frequency corresponding to the pavement surface, and repeating for each consecutive higher wavelength or lower frequency corresponding to a substantially horizontal layer along the predetermined penetrating depth, dividing the respective phase velocity value by a predetermined estimate of the amplitude of particle vertical displacement for the substantially horizontal layer, while assuming all deeper layers are uniform half-space, to derive estimates of shear velocity at corresponding penetrating depths, wherein the predetermined estimate of the amplitude of particle vertical displacement correlates dimensionless particle displacement with dimensionless depth, and
iteratively adjusting the estimates of shear velocity by repeating, starting at the lowest wavelength or highest frequency and for each consecutive higher wavelength or lower frequency corresponding to each substantially horizontal layer along the predetermined penetrating depth, the steps of dividing the respective phase velocity value by a predetermined estimate of the amplitude of particle vertical displacement for the substantially horizontal layer, while taking into consideration the derived estimates of shear velocity value, until convergence.

12. The system of claim 11, wherein the data processor further comprises a data acquisition unit for sampling the audio input signals and for generating a digital representation thereof.

13. The system of claim 11, further comprising a global positioning system receiver for providing location information to the data processor.

14. The system of claim 11, further comprising a trigger for enabling selective triggering of the point load impact subsystem.

15. The system of claim 11, wherein the data processor is further operative to calculate an inversion of the dispersion curve by correlating dimensionless particle displacement with dimensionless depth as the predetermined estimate of the amplitude of particle vertical displacement.

16. The system of claim 11, wherein the data processor is further operative to temporally window the received audio signals to eliminate direct acoustic noise resulting from the impact.

17. The system of claim 11, further comprising a sound barrier enclosure for each microphone of the array of microphones.

18. The system of claim 17, wherein the sound barrier enclosure comprises a substantially cylindrical enclosure having a first closed end, a second open end, and a cylindrical wall, the respective microphone being disposed within and coaxially with the substantially cylindrical enclosure.

19. The system of claim 18, wherein the exterior surface of at least one of the first closed end and the cylindrical wall is provided with a sound reflecting material.

20. The system of claim 18, wherein the interior surface of at least one of the first closed end and the cylindrical wall is provided with a sound absorbing material.

21. The system of claim 11, wherein each microphone of the array of microphones comprises a directional microphone having a respective acoustic axis substantially orthogonal to the pavement upper surface.

22. The system of claim 11, where the wheeled platform is a motor vehicle and the array of microphones is disposed on a lower surface thereof.

* * * * *